US008479409B2

(12) United States Patent  (10) Patent No.: US 8,479,409 B2
Johal  (45) Date of Patent: Jul. 9, 2013

(54) METHOD FOR DRYING SPENT FILTER MEDIA

(75) Inventor: Sarjit Johal, Iowa City, IA (US)

(73) Assignee: Grain Processing Corporation, Muscatine, IA (US)

( * ) Notice: Subject to any disclaimer, the term of this patent is extended or adjusted under 35 U.S.C. 154(b) by 1315 days.

(21) Appl. No.: 11/383,593

(22) Filed: May 16, 2006

(65) Prior Publication Data

US 2006/0254077 A1  Nov. 16, 2006

Related U.S. Application Data

(60) Provisional application No. 60/681,173, filed on May 16, 2005.

(51) Int. Cl.
*F26B 3/00* (2006.01)

(52) U.S. Cl.
USPC ............. 34/332; 34/338; 34/350; 34/402; 588/10; 264/117; 423/13; 432/138; 110/332; 431/328

(58) Field of Classification Search
USPC ............. 34/332, 338, 340, 350, 381, 402, 34/407, 413, 497; 588/9, 10; 264/117; 423/13; 976/DIG. 384, DIG. 393; 432/13, 138; 110/332; 431/328
See application file for complete search history.

(56) References Cited

U.S. PATENT DOCUMENTS

| | | | |
|---|---|---|---|
| RE17,212 E * | 2/1929 | Stockton | 241/17 |
| 1,914,484 A * | 6/1933 | Bunce et al. | 266/154 |
| 2,024,589 A * | 12/1935 | Lewers | 502/45 |
| 2,242,796 A * | 5/1941 | McKinley Stockton | 502/412 |
| 2,621,160 A * | 12/1952 | Johnson et al. | 432/13 |
| 2,698,815 A * | 1/1955 | Bishop | 427/215 |
| 3,078,164 A * | 2/1963 | De Lisle | 426/580 |
| 3,256,613 A * | 6/1966 | Moulthrop | 34/402 |
| 3,670,424 A * | 6/1972 | Hofer et al. | 34/340 |
| 3,683,511 A * | 8/1972 | Johnson et al. | 34/333 |
| 3,802,089 A * | 4/1974 | Stephanoff | 34/327 |
| 3,969,482 A * | 7/1976 | Teller | 423/235 |
| 4,014,104 A * | 3/1977 | Murphy | 34/350 |
| 4,138,337 A * | 2/1979 | Smith | 210/238 |
| 4,212,112 A * | 7/1980 | LaDelfa et al. | 34/338 |
| 4,254,557 A * | 3/1981 | Mayer et al. | 34/249 |
| 4,254,558 A * | 3/1981 | Mayer | 34/249 |
| 4,254,616 A * | 3/1981 | Siminski et al. | 60/39.12 |
| 4,255,166 A * | 3/1981 | Gernand et al. | 95/27 |
| 4,255,403 A * | 3/1981 | Mayer et al. | 423/244.06 |
| 4,263,163 A * | 4/1981 | Ross | 588/10 |
| 4,389,332 A * | 6/1983 | Ross | 252/378 R |
| 4,396,512 A * | 8/1983 | Beauman et al. | 210/668 |
| 4,434,060 A * | 2/1984 | Altmansberger et al. | 210/724 |
| 4,457,703 A * | 7/1984 | Ross | 432/13 |
| 4,500,363 A * | 2/1985 | Roehl | 134/10 |
| 4,529,497 A * | 7/1985 | Watson et al. | 208/419 |
| 4,579,525 A * | 4/1986 | Ross | 432/13 |
| 4,587,022 A * | 5/1986 | Shimizu et al. | 210/710 |
| 4,988,289 A * | 1/1991 | Coucher | 432/103 |
| 5,055,029 A * | 10/1991 | Avidan et al. | 431/7 |
| 5,096,415 A * | 3/1992 | Coucher | 432/14 |
| 5,234,877 A * | 8/1993 | Pinnavaia et al. | 502/84 |
| 5,311,671 A * | 5/1994 | Brooks et al. | 34/66 |
| 5,374,337 A * | 12/1994 | Ng et al. | 203/41 |
| 5,461,742 A * | 10/1995 | Pasad et al. | 8/149.2 |
| 5,656,178 A * | 8/1997 | Marchesi et al. | 210/770 |
| 5,678,236 A * | 10/1997 | Macedo et al. | 588/11 |
| 5,715,611 A * | 2/1998 | Jacobs et al. | 34/216 |
| 5,738,703 A * | 4/1998 | Bandurski | 71/9 |
| 6,110,361 A * | 8/2000 | Bower et al. | 210/181 |
| 6,261,604 B1 | 7/2001 | Tuefel | |
| 6,405,664 B1 * | 6/2002 | Logan et al. | 110/345 |
| 6,832,565 B2 * | 12/2004 | Chandran et al. | 110/345 |
| 6,883,444 B2 * | 4/2005 | Logan et al. | 110/345 |
| 6,997,118 B2 * | 2/2006 | Chandran et al. | 110/212 |
| 7,566,400 B2 * | 7/2009 | Harmon et al. | 210/631 |
| 8,420,042 B2 * | 4/2013 | Dickinson et al. | 423/445 B |
| 2002/0152937 A1 * | 10/2002 | Logan et al. | 110/341 |
| 2003/0196578 A1 * | 10/2003 | Logan et al. | 110/347 |
| 2003/0205531 A1 * | 11/2003 | Koslow | 210/660 |
| 2005/0120924 A1 * | 6/2005 | Chandran et al. | 110/203 |
| 2006/0254077 A1 * | 11/2006 | Johal | 34/332 |
| 2011/0190123 A1 * | 8/2011 | Apablaza Hidalgo et al. | 504/101 |

FOREIGN PATENT DOCUMENTS

JP  2005074334 A  * 3/2005

* cited by examiner

*Primary Examiner* — Steve M Gravini
(74) *Attorney, Agent, or Firm* — Fitch, Even, Tabin & Flannery, LLP

(57) ABSTRACT

Disclosed is a process of stabilizing spent filter material that comprises mixing the filter media with a dry media to produce a composition having a moisture content that is sufficiently low to retard microbial growth. The composition comprises spent filter media and a dry material, and preferably comprises diatomaceous earth. Soil is treated by adding the composition as a top dressing, soil amendment, or the like.

17 Claims, No Drawings

METHOD FOR DRYING SPENT FILTER MEDIA

RELATED APPLICATION

This application claims priority to prior provisional application Ser. No. 60/681,173, filed May 16, 2005. The entire contents of this application are hereby incorporated by reference in their entireties.

FIELD OF THE INVENTION

The invention relates to methods for treating spent filter media, in particular filter media containing diatomaceous earth. In other embodiments, the invention pertains to compositions that contain spent filter media, and to associated methods. The compositions of the invention are useful in various embodiments as top dressings, soil amendments, and fertilizers in lawn care applications.

BACKGROUND OF THE INVENTION

Vacuum filtration is commonly used in the manufacture of a variety of agricultural, food, beverage, and biotechnology industries. In addition to the fixed equipment, production scale vacuum filtration systems such as rotary drum vacuum filters, leaf filters, and the like typically employ process aids, which are also referred to as filtration aids. These consumable aids range from fibers, cloths, and the like to particle materials such as clays, diatomaceous earth, carbon, cellulosics and associated materials and are used to coat the filters. These materials retain both insoluble and soluble impurities by various physicochemical means. Particulate materials are also sometimes added to the prefiltration supernatants and subsequently recovered from the filter as a high moisture filter cake as it accumulates on the filter surface. A number of permutations of this approach are practiced in an array of industries today. For example, diatomaceous earth (DE) is a widely used filter medium. Diatomaceous earth is frequently used, alone or in conjunction with other process aids, to clarify water, beverages including beers, wines, juices and the like, and also to clarify food ingredients such as maltodextrins, syrups and the like.

An undesirable and problematic aspect of filtration systems that employ a filtration aid is the disposal of the used (spent) filtration aid. Because of the significant cost and time entailed in the recycling of filtration aids, generally the spent filter media is simply disposed of in a landfill. However, disposing of this media in a landfill is wasteful and unproductive.

Materials that can be used in filtering aids often have other functionalities and utilities. Diatomaceous earth also is widely used in gardening, landscaping, and potting soil mixes. Diatomaceous earth also is used as a non-toxic, organic insecticide, where it is regarded as a safe alternative to chemical insecticides. For these applications, the diatomaceous earth is typically added as a dry mined powder. The diatomaceous earth is typically added to the final gardening, landscaping, and potting soil mix and dry blended. In these applications, the diatomaceous earth typically is devoid of biomolecules such as carbohydrates and proteins or other extraneous matter.

Diatomaceous earth found in spent filter media is generally not suitable in such lawn and garden applications. The spent filter media contains a significant amount of water, and generally also contains particulates and other material such as carbon and nutrients retained from the filtration stream. If the filter media is not dried or preserved immediately, uncontrolled microbial growth can occur in the presence of the media. Such microbial growth generally will render the media unsuitable for lawn and garden applications. Diatomaceous earth may be dried, but known drying processes are deemed to be uneconomical in lawn and garden applications. Moreover, organic material entrapped in the diatomaceous earth often is undesirable. For example, organics are deemed undesired in potting soil mixes and seed bedding soils.

Other approaches such as composting (as purportedly disclosed in U.S. Pat. No. 6,261,604) have been suggested, but these approaches have not been widely adapted. Composting is a slow, laborious process that requires substantial time and space. Moreover, although composting does address some broad disposal issues, composting does not significantly enhance the utility of the media.

Thus, the absence of a technology to efficiently recycle spent filter media reduces its value and causes users to incur disposal expense.

The Invention

It has now been found that spent filter media, such as diatomaceous earth, may be stabilized by blending the filter media with a dry material to form a composition. A preferred source of dry material is lime, but other ingredients, such as clays, binders, surfactants, minerals, fibrous plant materials, or fertilizer ingredients that contribute plant nutrients or micronutrients may be used in conjunction with the invention. The moisture content of the composition is preferably sufficiently low to inhibit mold growth, and in preferred embodiments of the invention is below 18% by total weight. The composition preferably is provided in the form of discrete plural particles, the particles taking the form of pellets or granulated particles.

The resulting composition, which preferably is biodegradable and non-toxic is useful in many commercial applications. In particular, the inventive composition has utility in turf, landscape, gardening and agronomic and/or horticultural applications, such as top dressing treatments, fertilizers, and soil amendments. The invention is deemed in preferred embodiments to find utility in highly chemically treated soil where the microbial population/density is depleted. For many such applications, entrapped organic and biological materials are believed to enhance the functionality and value of the composition.

In many lawn and garden applications, materials such as peat moss, vermiculite, and perlite are used to provide soil aeration. Soil aeration compositions made with such materials are generally more expensive than those prepared in accordance with the preferred embodiments of the invention. The composition of the preferred embodiments of the invention may be used to provide soil aeration more inexpensively than can be attained using the heretofore described materials.

Methods of preparing a composition and methods of use of such composition, such as those described in more detail hereinbelow, also fall within the scope of some of the various embodiments of the invention.

DETAILED DESCRIPTION OF THE PREFERRED EMBODIMENTS

It has been discovered that spent filter media, such as media containing diatomaceous earth, can be processed directly as it is shed from the filtration system. Although the present invention is contemplated to be applicable to any suitable type of spent filter media, spent filter media that contains diatomaceous earth (such as that obtained from a commercial brewing process) is the preferred embodiment. In such cases, the filter media often will include other processing aids, such as carbon, ion-exchange materials, surfactants and the like, in addition to diatomaceous earth. Preferably, 30 wt % or more of the composition, based on the dry weight of the ingredients in the spent filter media, comprises diatomaceous earth. Typically, the spent filter media will contain about 30 to 95 wt % diatomaceous earth, about 10 to 50 wt % organic carbon, about 1 to 25 wt % activated carbon and about 20 to 50 wt % water. Because the invention is deemed to be particularly applicable to such spent filter media, the invention is usually described herein with reference to same, although it is contemplated that a homogeneous spent filter medium (in particular exclusively diatomaceous earth) is useful in conjunction with the invention.

As supplied, spent filter media most typically contains 20 to 40 total wt % water. In accordance with one embodiment, the present invention is directed to a process of drying the spent filter material by forming a composition that includes the spent filter media and a dry material, the composition having to a moisture content that is sufficiently low to prevent microbial growth during storage of the composition. In preferred embodiments, the composition includes at most 18% water by total weight; more preferably, the composition includes at most 15% water by total weight; most preferably, the composition includes 10%-15% water by total weight.

The filter media is blended with a dry material to form a composition. Any suitable dry material may be used in conjunction with the invention, and materials such as calcium carbonate, clays, lime, or the like may be employed. When one of the foregoing calcium-containing materials is employed, it may be, and preferably is, applied in the form of lime, an ingredient that is beneficial in that it is useful in adjusting the pH of certain soils. Agricultural lime generally comprises limestone crushed to a fine powder. Alternatively, calcium carbonate may be obtained from other sources, such as shells. Clays are particularly advantageous in that many clays serve to correct soil acidity. Mixtures of the foregoing or other suitable materials may also be used.

Prior to blending with the spent filter media, the dry material need not be completely moisture-free, and in typical embodiments the dry material includes some moisture but is sufficiently low in moisture to dry the spent filtration medium to the requisite level of dryness. The dry material preferably includes less than 2 wt % moisture, and more preferably less than 1 wt % moisture, based on the total weight of the dry material.

The dry material and spent filter media may be blended in any suitable fashion and in any ratio effective to dry the spent filter media to the desired moisture content, which generally is an amount that will not support microbial growth. The dry material and spent filter media, along with other desired ingredients, are blended to produce a composition containing 5% to 90 wt %, preferably 40% to 70%, more preferably 40 to 60%, spent filter media based on dry solids weight. Typically, the dry material is present in amounts of about 15 and 60 wt % based on the total weight of the filter media and the dry material.

Other ingredients may be incorporated into the dried composition. For instance, the composition may include binders, such as iron lignosulfonate or another lignosulfonate. Iron lignosulfonate, used as a binder, also provides the soil with mineral iron. When used, the binder should be added in amounts effective to attain a binding effect, typically about 2 to 30 wt % based on the total weight of the dried composition. Alternatively, or in addition thereto, the composition may include a surfactant. Natural surfactants, such as yucca extract, are preferred. When used, the surfactant should be added in any amount effective as a surfactant. In the case of yucca extract, 0.05 to 1.5 wt % yucca extract is added, typically about 0.3 wt %, based on the total weight of the dried composition.

One or more additional plant materials may be incorporated into the composition. such as corn fiber, alfalfa and the like. These materials preferably are added after the dry material and diatomaceous earth are blended. Such materials are deemed suitable as pelletizing aids when the composition is supplied as a pelletized composition, and may be added in amounts suitable therefor. Some such materials, such as alfalfa, provide additional nutritive benefit to the composition.

In some embodiments, the dry material comprises or incorporates an additional plant nutrient. Useful plant nutrients include but are not limited to urea, phosphate, and other macro- and micro-nutrients. When used to augment another dry material, the plant nutrient may be present in any suitable amount effective to obtain the desired organic or nutritive value. One suitable nutrient is SOLULAC™, sold by Grain Processing Corporation of Muscatine, Iowa. SOLULAC™ comprises corn fiber augmented with distillers grain solubles. When used, typical amounts of SOLULAC are about 2 to 30 wt %, based on the total weight of the composition.

When intended as a fertilizer, the composition may include any suitable ingredients. Preferred ingredients include nitrogenous materials, such as urea. Such materials may be present in any suitable amounts.

A composition prepared as discussed hereinabove may be provided to a user in any suitable form. For instance, the composition may be provided as a powder or "meal," prepared simply by blending the above-described ingredients. Preferably, however, the composition is provided in the form of pellets, by which is contemplated the pellets made using a conventional pelleting mill or similar apparatus that adds heat and/or mechanical energy in an extrusion process. During the pelleting process, heat may be added as needed to facilitate pelleting. The pelleted material is then cooled and, preferably, the particle size is reduced, such as by crumbling. Upon pelleting, the preferred particle size is about 7-20 mesh and more preferably 9-12 mesh. The moisture content of the pellets so prepared is preferably 10% or lower. Alternatively, the product may be provided in the form of granulated particles prepared with a suitable binder.

The invention is also directed to a method of treating soil. The method comprises adding to the soil a composition comprising spent filter media and a dry material as discussed hereinabove. The composition may be added as a fertilizer, a top dressing, or a soil amendment. A pelleted product prepared in accordance with the foregoing teachings is particularly suitable for use as a top dressing. The top dressing may be applied by spreading the composition onto a surface using any suitable apparatus and in any amount desired, such as an amount effective to inhibit insecticidal growth on the soil, to aerate the soil, or to add nutritive value to the soil. The pelleted product may be spread in amounts ranging, for instance, from 0.5 lb/1000 sq. ft. to 60 lb/1000 sq. ft. One suitable spreading apparatus is a rotary spreader. Alternatively, the composition may be applied after manually aerating a soil bed or turf area.

The following non-limiting examples are provided for illustration.

EXAMPLE 1

A spent filter material (filter cake) was recovered from a rotary vacuum filter. The filter material contained about 35%

DE, 22% organic carbon, 12% activated carbon and 31% water. The filter material was added to a laboratory mixer and homogenized. About 20% calcium carbonate was then added, and the mixture thus formed was thoroughly blended.

After a few minutes of further mixing, a dry animal feed product, SOLULAC™ (Grain Processing Corp., Muscatine, Iowa) was added in an amount of about 20% by weight of the mixture. The final composition contained about 60% filter cake, 20% calcium carbonate and 20% SOLULAC A meal was formed. The moisture content of the meal was about 15.5%.

The meal thus prepared was pelleted using a pilot scale pellet mill. The moisture content of the pellets was about 14%. After cooling overnight on a flat surface, the moisture content of the pellets was about 4.7%. The pellets were packed in 5-gallon pails.

EXAMPLE 1A

Example 1 was repeated up to the point of formation of a meal, except that corn bran was used instead of SOLULAC. The moisture content of the meal was 12.5%

EXAMPLE 2

A spent filter cake comparable to the material used in Example 1 (DE, carbon and entrapped organics) was incorporated in a composition as follows:

| | |
|---|---|
| Spent filter cake | 50% |
| SOLULAC | 10% |
| Fe Lignosulfonate | 20% |
| Calcium Carbonate | 19.7% |
| Yucca Extract | 0.3% |

As in Example 1, the composition, which had a moisture content of about 12.7%, was thoroughly blended and pelleted using a pilot scale pellet mill. The pellets exhibited good integrity and hardness. The pellets were cooled overnight and available for packaging the next day.

EXAMPLE 3

A composition was prepared as follows:

| | |
|---|---|
| Spent filter cake* | 40% |
| SOLULAC | 10% |
| Powdered Lime | 49.7% |
| Yucca Extract | 0.3% |

*composed of DE, carbon, and organics

The components were blended and pelleted as in Examples 1 and 2.

EXAMPLE 4

The meals of Examples 1, 2 and 3 were pelleted using a pilot California Pellet Mill. The compositions, which typically ranged from 15% to 13% moisture, were blended and fed into the mill as is. A pellet die with 0.156 times 1 inch openings was employed. The pelleting temperature was 83-85° C. The temperature of the pellets immediately recovered from the mill was about 118° C. The hot pellets were then collected and cooled overnight at room temperature. The final pellet moisture ranged from 5% to 9%.

EXAMPLE 5

Spent filtration material from Grain Processing Corporation (Muscatine, Iowa) was collected and delivered to a production scale, fully integrated mixing-pelleting and finishing line. The spent material was transferred to a large mixing vessel, generally from 12-36 hours after delivery.

Dry calcitic limestone (1-2% moisture) was added to the vessel containing the spent filter cake. This mixture was mixed for at least 30 minutes (longer blending times being preferred to provide greater homogeneity and to reduce the formation of aggregates). After achieving a relatively uniform mixture, and while still mixing, alfalfa meal was added to the mixer. The spent filter cake, limestone and alfalfa meal mixture was then blended for at least another 30 minutes. The blended composition, which was composed of approximately 60% spent cake, 20% limestone/calcium carbonate and 20% alfalfa meal, was conveyed to a commercial feed pelleting line.

The mixture was pelleted using a 3/12" pellet die. No steam or extraneous heat was added during the pelleting process. The formed pellets were cooled for about 20-25 minutes using an ambient temperature, unconditioned air chamber (commonly referred to as a pellet "conditioner"). The pellets then were conveyed to crumbling machine, commonly referred to a "pellet crumbler," which used rollers to reduce the pellets to a smaller particle size within the heretofore expressed preferred range.

The finished product, which had a moisture content of about 10%, was transferred to holding vessels to await packaging. This product contained activated carbon by virtue of the carbon present in the original spent filter media.

EXAMPLE 6

A fertilizer is prepared using dried spent filter media and urea.

It is thus seen that the present invention provides a method for drying spent filter media and a dried composition prepared upon drying the spent filter media. The process of the instant invention provides recycling and adds value to what otherwise would be a waste filter product. The composition has utility in a variety of agricultural and landscaping applications, as well as soil and compost products. The composition is stable and resistant to spoilage and odor formation, and allows nutrients entrapped in the filter media and other materials present in the composition to be delivered to soil in numerous applications. In addition, the composition improves soil attributes such as porosity, drainage, and the like. The invention thus provides a composition that may substitute for more expensive materials, such as peat moss.

All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. No language in the specification should be construed as indicating any non-claimed element as essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method of treating soil comprising adding to the soil a composition comprising spent filter media and a dry material, wherein the spent filter media comprises spent diatomaceous earth and wherein the composition comprises at most 15 wt % water.

2. The method of claim 1 wherein the composition is added as a top dressing.

3. The method of claim 1 wherein the composition is added as a soil amendment.

4. The method of claim 1, said filter media containing about 30 to 95 wt. % spent diatomaceous earth, about 10 to 50 wt. % organic carbon, about 1 to 25 wt. % activated carbon and about 20 to 50 wt. % water.

5. The method of claim 1, said binder comprising a lignosulfonate.

6. The method of claim 1, said dry material comprising corn fiber and distillers grain solubles.

7. A method for soil aeration comprising adding to soil a composition comprising a dried spent filter media composition, said composition having been prepared by mixing the filter media with a dry material to produce a composition having a moisture content that is sufficiently low to inhibit microbial growth in the composition; wherein the spent filter media comprises spent diatomaceous earth.

8. A method according to claim 1, wherein the dry material is at least one selected from the group consisting of calcium carbonate and clay.

9. A method according to claim 1, wherein the dry material is lime.

10. A method according to claim 1, said spent filter media in said composition comprising diatomaceous earth, organic carbon, and activated carbon.

11. A method according to claim 7, said composition comprising a binder in an amount of 2 to 30% by weight based on the total weight of said composition.

12. A method according to claim 11, said binder comprising a lignosulfonate.

13. A method according to claim 7, said dry material comprising corn fiber and distillers grain solubles.

14. A method according to claim 7, said dry material being present in the amount of from 2 to 30 wt. % based on the total weight of the composition.

15. A method according to claim 7, wherein the dry material is at least one selected from the group consisting of calcium carbonate and clay.

16. A method according to claim 7, wherein the dry material is lime.

17. A method according to claim 7, said spent filter media in said composition comprising diatomaceous earth, organic carbon, and activated carbon.

* * * * *